United States Patent [19]

Palumbo

[11] 4,370,978

[45] Feb. 1, 1983

[54] KNEE BRACE

[76] Inventor: Pasquale M. Palumbo, 906 Frome La., McLean, Va. 22101

[21] Appl. No.: 313,674

[22] Filed: Oct. 21, 1981

[51] Int. Cl.³ ............................................. A61F 3/00
[52] U.S. Cl. .................................. 128/80 C; 128/165
[58] Field of Search .................. 128/80 C, 165; 2/22, 2/24

[56] References Cited

U.S. PATENT DOCUMENTS

| | | | |
|---|---|---|---|
| 1,092,836 | 4/1914 | Hart | 2/22 |
| 1,388,772 | 8/1921 | Sheehan | 128/165 |
| 1,622,211 | 3/1927 | Sheehan | 2/22 |
| 2,270,685 | 1/1942 | Miller | 128/165 |
| 4,116,236 | 9/1978 | Albert | 128/80 C |

Primary Examiner—John D. Yasko

[57] ABSTRACT

A knee brace useful in treatment and diagnosis of patella subluxation, chondromalacia, and inflamatory conditions and strains of the extensor mechanism of the knee. The brace includes two para-patellar pads which function to stabilize the patella, an infra-patellar ligament pad which applies direct pressure to the patellar ligament and a supra-patellar and an infra-patella live elastic straps which apply compressive forces to the quadriceps mass and to the patellar ligament to diminish shocking, compression and tensile forces to the extensor mechanism.

9 Claims, 5 Drawing Figures

KNEE BRACE

BACKGROUND OF THE INVENTION

The present invention relates to knee support devices, and more particularly to a knee brace device intended to stabilize the patella in a manner useful in the treatment and diagnosis of extensor mechanism problems of the knee, including patellofemoral chondromalacia, patellar ligament tendonitis and Osgood-Schlatter's disease of the knee.

It is well known that individuals frequently develop various pathological problems with their knees, particularly when these individuals are active in physically strenuous endeavors such as athletic activities, e.g. contact sports and jogging. The most commonly occurring problems relate to excessive compression forces, abnormal patellofemoral motion stretching or tearing of the various knee ligaments, injury to the cartilaginous articular surfaces of the knee joint and fractures.

Patellar subluxation or abnormal and undesirable movement of the patella, laterally, relative to its normal up and down movement in the vertical tract defined by the trochlea can precipitate the onset of chondromalacia or aggravate existing chondromalacia of the patella. Related pathological conditions of the knee which commonly occur are patellar ligament tendonitis, patellar tendon tendonitis and Osgood-Schlatter's disease.

Also, operative procedures of the knee, particularly arthroscopie procedures, are especially painful, and post-operative knee bracing, particularly with patella stabilization, tends to diminish the pain and improve the operative result.

As noted, problems peculiar to the extensor mechanism apparatus of the knee comprise only a portion of all common problems of the knee, and several unrelated or partially related problems of the knee may occur simultaneously, particularly in individuals having loose ligaments, when engaged in relatively strenuous activities, such as athletic activities involving the knee.

Others have devoted attention and proposed various knee braces and supports directed to general problems of the knee. For example, Spiro, U.S. Pat. No. 3,473,527; Lehman, U.S. Pat. No. 3,804,084; and Moore, U.S. Pat. No. 3,853,123, have proposed various knee support, brace, and knee splinting devices intended to restrain the knee to prevent normal knee flexion or movement. Such devices are directed generally to the problem of immobilizing the knee as a whole, and do not provide knee bracing during normal knee flexion and extension. Nirschel, U.S. Pat. No. 3,926,186 and Stromgren, U.S. Pat. No. 3,945,046, propose other muscular and flexible knee supports. Nirschl's apparatus, however, is not designed to provide medial-lateral stabilization of the patella and is inherently incapable of performing a dynamic bracing function for the knee. Stromgren's apparatus, on the other hand, is directed to the general problem of providing stability to the medial knee ligament complex. Detty, U.S. Pat. No. 4,084,584 discloses a simple knee sleeve device which includes a pad and which is capable of providing limited, static patellar bracing when, for example, the knee is passive, i.e., when the knee is not in motion or when the knee in a single position or within a narrow range of positions. Barlow, U.S. Pat. No. 4,250,578 discloses a protective knee support apparatus. The Applicant herein, by U.S. patent application Ser. No. 949,121, filed Oct. 6, 1978, for a Dynamic Patellar Brace, now abandoned; Continuation application Ser. No. 153,708, filed May 27, 1980 for Dynamic Patellar Brace, now U.S. Pat. No. 4,296,744 has provided a patellar brace useful for both diagnosis and treatment of patellar subluxation.

SUMMARY OF THE INVENTION

Accordingly, an object of the present invention is to provide a knee brace useful for both treatment and diagnosis of extensor mechanism problems of the knee, and certain problems of the knee related to or aggravated by extensor mechanism problems.

A further object of the invention is to provide a knee brace capable of performing its bracing, splinting or stabilizing function for the patella to accomplish the foregoing purposes during the full normal range of knee flexion, extension, rotation, and movement.

A still further object of the invention is to provide a knee brace which functions to diminish the level of potentially harmful shocking, compression and tensile forces applied to the knee when the brace is in use.

A still further object of the invention is to provide a knee brace to facilitate proper and positive diagnosis of extensor mechanism problems of the knee, particularly when such problems exist in their milder forms when their clinical presentation simulates that of other pathological conditions of the knee.

A still further object of the present invention is to provide a knee brace suitable for post-operative use.

A still further object of the invention is to provide a knee brace which is relatively simple to put in place and use, and which will provide knee bracing without need for constant adjustment or readjustment.

A still further object of the invention is to provide a knee brace which can be utilized with minimal discomfort, without being unsightly, and without requiring the user to utilize crutches or to walk in an unnatural manner.

A still further object of the invention is to provide a knee brace having a relatively simple construction, and which is relatively simple to manufacture.

Toward the fulfillment of these and other objects, the present invention includes two para-patella pads which function to stabilize the patella, particularly in the lateral direction, an infra-patella strap, a small patellar ligament pad which applies direct pressure to the patellar ligament, and a supra-patella strap, each of which straps preferably consists of live elastic or elastomer material. The knee brace apparatus is preferably attached to an elastic sleeve adapted to have the leg inserted therethrough and to have the knee positioned therein in use. The brace functions to stabilize the patella throughout the full normal or physiologic range of knee flexion, rotation, extension and movement, and to diminish the level of potentially harmful shocking, compression and tensile forces applied to the knee when the brace is in use.

DESCRIPTION OF THE PREFERRED EMBODIMENTS

Figure 1:
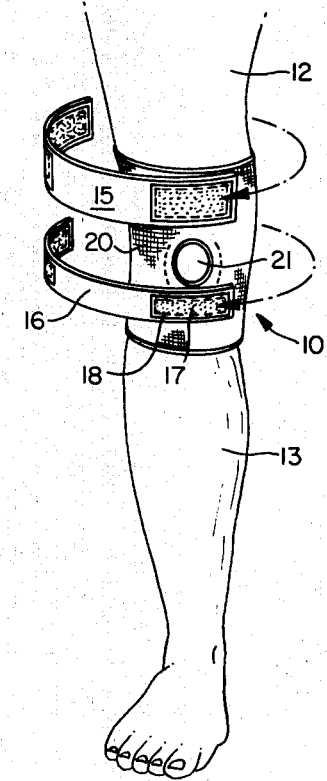
FIG. 1 is a perspective view of the knee brace according to the present invention positioned on the knee and ready to have the elastic strap or arm members thereof wrapped circumferentially about the knee.

As shown in FIG. 1, a knee brace 10 according to the present invention is positioned between the upper portion 12 and the lower portion 13 of the leg of the user (not shown). The knee brace includes an elastic sleeve 20 through which the lower portion 13 of the user's leg has been inserted to facilitate positioning of the brace 10 on the user's knee.

The elastic sleeve 20 includes an opening, aperture, or patellar cutout 21 in the wall thereof which is preferably positioned over or about the patella or kneecap by the user when the leg is inserted through the elastic sleeve 20 so that the patella is in registration with the opening when the brace is in use. This arrangement is designed to facilitate proper positioning of the brace by the user and to avoid application of a compressive force directly to the patella.

Figure 2:
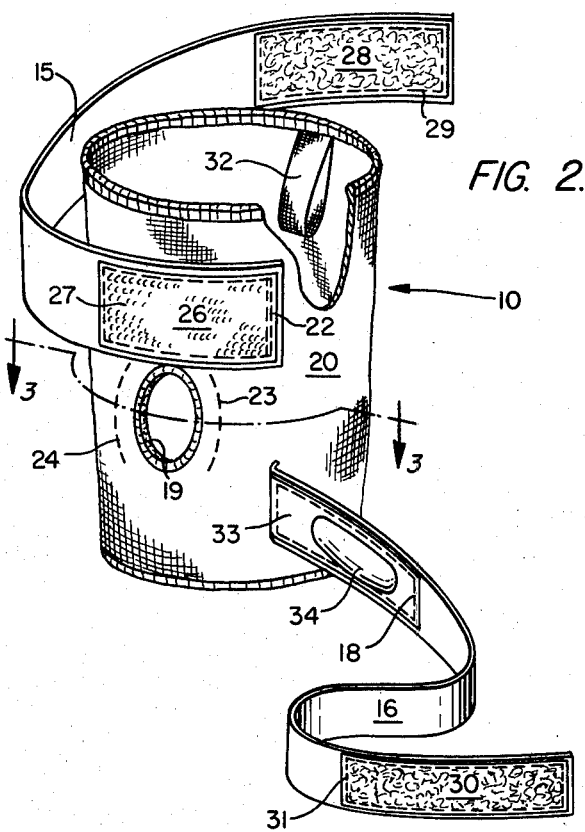
FIG. 2 is a perspective view, partially fragmentary, of the knee brace of FIG. 1.

As further shown in FIG. 1, the knee brace includes two elastic arm or strap members 15, 16 formed in an elastic band-like shape which are adapted to be wrapped circumferentially about the upper leg 12 and the lower leg 13, respectively, as shown by the arrows in FIG. 1 when the knee brace is in use. One end of each of the elastic arm members 15, 16 is attached to the sleeve 20 as will be described. As shown in FIGS. 1 and 2, the elastic arm member 15, 16, includes thereon fastening and holding means 26 and 17, respectively, which preferably comprise Velcro strip means, which are attached to the elastic arm members 15, 16 on the outer band surfaces thereof near where the arm members 15, 16 are attached to the elastic sleeve 20. Cooperating fastening and holding means 28, 30, also preferably Velcro means, are associated, respectively, with the elastic arm members 15, 16 and are attached to the inner band surfaces thereof, respectively, near the ends thereof furthest removed from the point of attachment of the arm members 15, 16 to the elastic sleeve 20 as shown.

Figure 5:
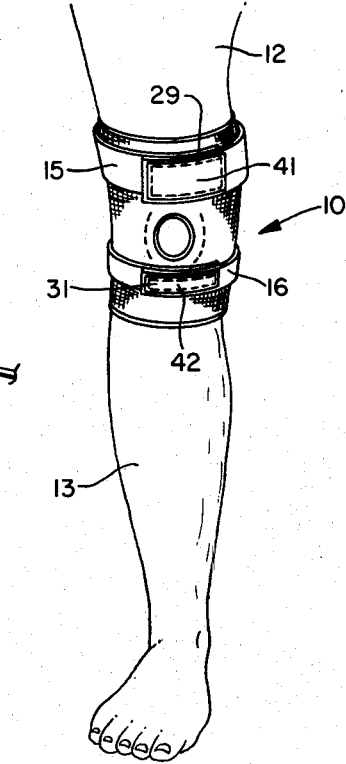
FIG. 5 is a further perspective view similar to FIG. 1 but showing the elastic arm or strap members wrapped and held in the wrapped position when the knee brace is in use.

Preferably, the respective fastening and holding means 17, 26, 28, 30 are fastened to the respective arm member by stitching or other suitable attachment means, such as stitching means 18, 27, 29, 31, respectively, as shown in FIGS. 1 and 2. Other attachment means such as pliable adhesive means could be used in lieu of stitching means as shown. It has been found useful to use thin pieces of reinforcing material 41, 42 on the outer band surfaces of the arm members 15, 16 to receive and better hold the stitches 29, 31, respectively, as shown in FIG. 5.

Figure 3:
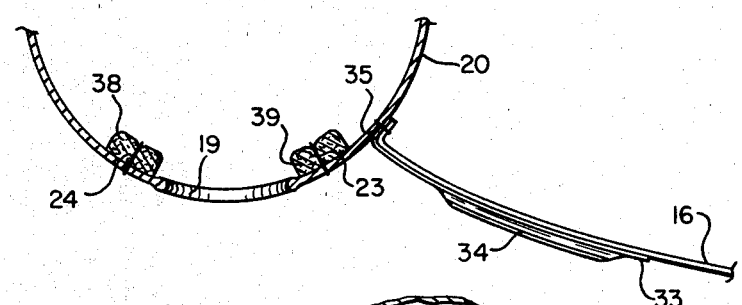
FIG. 3 is a sectional view of a portion of the knee brace of the present invention taken through line 3—3 in FIG. 2.

The attachment of the respective elastic arm members 15, 16 to the elastic sleeve 20 is achieved, preferably, by additional stitching 22, 35, respectively, as shown in FIGS. 2 and 3. Alternate means are possible for this attachment; for example, it is possible for the arm members 15, 16 to be detachably attachable to the elastic sleeve 20 by Velcro means (not shown).

The elastic arm members 15, 16 are preferably constructed from a live elastic or rubber material, such as by cutting strips or bands from a sheet of such material.

Figure 4:
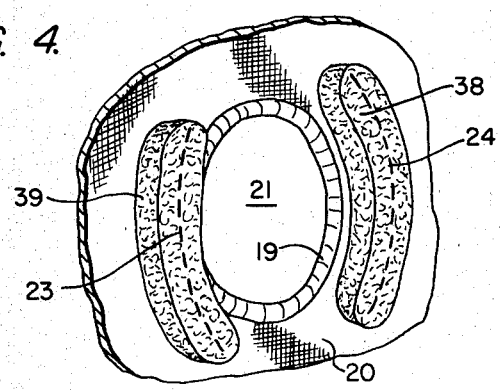
FIG. 4 is a partially fragmentary, perspective view showing the two para-patellar pads of the knee brace of the present invention.

The knee brace also includes two para-patellar pads 38, 39 attached to the surface of the inside wall of the elastic sleeve member 20 by stitching means 24, 23, respectively, as shown in FIGS. 2, 3, and 4. The para-patellar pad means are preferably made from felt material, foam rubber or the like and are arranged to be attached by stitching means 23, 24 to the elastic sleeve member 20, each in an arcuate or crescent shape, concave toward the patella cutout 21, on the inner surface of the elastic sleeve member 20 on either side of the edge 19 of the appature or patella cutout 21. Materials other than felt, and attachment means other than stitching can, of course, be used. With this arrangement, the two para-patellar pads 38, 39 function to brace or stabilize the patella laterally, i.e., in both the medial and lateral directions when the brace is in use (such as shown in FIG. 5) as will be further explained.

The two para-patella pads 38, 39 are particularly useful in cases of patella instability where abnormal lateral sheer stresses are created with flexion and extension of the knee. These abnormal stresses frequently cause stretching of the medial and lateral retinaculum causing pain and tenderness in those areas of the knee. By stabilizing the patella with the para-patellar pads 38, 39 of the knee brace 10, and with compressive forces applied to the quadriceps by the wrapped arm members 15, 16, the amount of abnormal lateral stress and motion is greatly diminished, thereby diminishing the stretching effect on the capsular structures, and thereby diminishing pain and tenderness in these areas of the knee. As a result, pain associated with chondromalacia of the patellofemoral joint is reduced and the progression of chondromalacia is diminished. Compression provided by the para-patellar pads 38, 39, the sleeve 20, and wrapped arm members 15, 16, also tend to discourage the formation of effusion.

As shown, the knee brace 10 of the present invention includes two live elastic straps 15, 16, one being a suprapatellar strap or arm member 15, and the other being the infra-patellar strap or arm member 16. The infra-patellar strap or arm member 16 includes on the inner band surface thereof, a patellar ligament pad 34 which is adapted to apply direct pressure to the patellar ligament when the brace is in use (such as shown in FIG. 5). The patellar ligament pad could also be formed directly on or directly attached to the sleeve 20 in an appropriate position thereon (not shown).

The patellar ligament pad 34 is preferably made from felt, foam rubber or similar material (not shown) which is sandwiched between a sheet of thin pliable leather or other suitable material 33 and the inner band surface of the elastic arm member 16, and fastened there-between by stitching means 18. Pliable adhesive means could also be used for this fabrication. With this fabrication, it is possible for the user of the brace 10, by manual manipulation, to exercise some control over the shape of the patellar ligament pad 34 itself. In normal use, the ligament pad 34 has a generally rectangular shape with rounded corners and smoothed edges as shown in FIGS. 2 and 3.

A label 32 may be included in the sleeve 20 to include pertinent information such as the size of the particular knee brace 10.

In use, the knee brace 10 of the present invention is first positioned on the knee with the patellar cutout or aperture 21 in registration with the patella, so that the two para-patellar pads 38, 39 are positioned to function to stabilize the patella in the medial and lateral directions. The supra-patellar and infra-patellar straps 15, 16, respectively, are then wrapped circumferentially about the knee, and the cooperating fastening and holding means 26, 28 and 17, 30 thereof, respectively, are engaged with one another as shown in FIG. 5 to hold those straps in the wrapped positions, thereby applying compressive forces to the quadriceps mass, and, with the cooperation of the patellar ligament pad 34, to the patellar ligament to diminish the level of shocking compression and tensile forces which would otherwise be applied to the components of the extensor mechanism. As noted, when the knee brace 10 is thus applied to the knee, the patellar ligament pad 34 applies direct pressure to the patellar ligament, thereby absorbing a portion of the shocking tensile or traction stresses placed upon the extensor mechanism, including the patellar tendon, the patella, the patellar ligament and the insertion of the patellar ligament at the tibilar tubercle. As a result, much of the shocking traumatic compressive and tensile forces are absorbed by the combination with the two constricting live elastic strap or arm members, 15, 16 thereby diminishing the stress on these structures as well as diminishing these potentially harmful forces at the patellofemoral level.

The absorption of these stresses at the patellofemoral level as well as at the level of the patellar tendon, ligament and retinaculae results in diminished trauma to those areas of the knee structure when the brace 10 is used. As a result of the diminished traumatic and tensile forces to the ligament, as well as the diminution of compression forces at the patellofemoral level, pain and tenderness to these structures are also reduced. These features of the knee brace 10, and the cooperation of these features also prevent abnormal excursion of the patella during flexion throughout the normal range of flexion, extension and rotation of the knee, thereby aiding in the prevention of patellofemoral chondromalacia as well as tendonitis of the patellar tendon, ligament and retinaculae. The knee brace 10 is also useful in the treatment of Osgood-Schlatter's disease of the knee, and post-operatively, after surgery on the knee.

The two para-patellar pads, one on each side of the patella, serve to brace or stabilize the patella laterally, while the circumferentially wrapped straps above and below the patella absorb a significant portion of the shocking effect, particularly noted during heel strike which results when the foot contacts the ground during walking, running, or descending stairs. The straps serve to absorb a portion of the shock going to the extensor mechanism of the knee and thereby absorb some of the stresses in the knee, resulting in a lesser portion of the stress applied to the patella being compressed into the femoral condyle, as well as less tensile forces at the patellar tendon and patellar ligament.

In clinical observation, individuals with chondromalacia who have tested the knee brace 10 report significant relief when walking, running, and ascending and descending stairs.

As noted, the knee brace 10 of the present invention is also of use in diagnosing problems of the knee. For example, a patient reporting a knee problem that is difficult to precisely diagnose can be requested to try or wear the knee brace 10, and depending on the type of improvement, if any, reported by the patient after undergoing predetermined exercises while wearing the brace, information useful in diagnosis of the particular knee problem(s) can be obtained.

Accordingly, it is seen that the knee brace according to the present invention accomplishes the above-described objects as well as other objects which will be apparent to those skilled in the art who will also appreciate that various modifications and changes may be made to the present invention without departing from the scope of the invention as defined in the appended claims.

What is claimed is:

1. A knee brace for stabilizing a patella throughout the normal range of flexion and movement of the knee comprising:

a sleeve member;

a first arm member, the first end of which is adapted to be circumferentially wrapped about the knee above the patella, the second end of which is attached to said sleeve member;

first and second means for bracing the patella attached to said sleeve member and adapted to be positioned medially and laterally of the patella when the brace is in use to stabilize the patella;

a second arm member, the first end of which is adapted to be circumferentially wrapped about the knee below the patella, the second end of which is connected to said sleeve member; and third means for bracing the patellar ligament operatively associated with said second arm member and adapted to apply direct pressure to the patellar ligament when the brace is in use.

2. A knee brace according to claim 1 wherein said second arm member comprises a strap member, having an inner surface and an outer surface, and wherein said third means for bracing the patellar ligament is formed on the inner surface of said strap member.

3. A knee brace according to claim 1 wherein said sleeve member has an opening formed in the wall portion thereof; and wherein said first and second means for bracing the patella are disposed on opposite sides of said opening and formed on the inner wall surface of said sleeve member.

4. A knee brace according to claim 3 wherein said second arm member comprises a strap member having an inner surface and an outer surface, and wherein said third means for bracing the patellar ligament is formed on the inner surface of said strap member.

5. A knee brace according to claims 2 or 4 wherein said means for bracing the patellar ligament is a pad.

6. A knee brace according to claims 3 or 4 wherein each of said first and second means for bracing the patella is an arcuately shaped pad, each of which is concave towards the patella when the brace is in use.

7. A knee brace according to claims 1, 2, 3 or 4 wherein said sleeve member comprises an elastic material and is adapted to have the knee positioned substantially within said sleeve member when the brace is in use.

8. A knee brace according to claims 3 or 4 wherein said sleeve member comprises an elastic material and is adapted to have the knee positioned substantially within said sleeve member with the patella in registration with said opening when the brace is in use.

9. A knee brace according to claims 1, 2, 3 or 4 further comprising means operably associated with said first and second arm members for holding the first ends thereof after circumferential wrapping thereof for preventing the unwrapping of said arm members when the brace is in use.

* * * * *